United States Patent [19]

Apffel

[11] Patent Number: 4,597,788
[45] Date of Patent: Jul. 1, 1986

[54] PROCESS FOR RECOVERING ETHANE, PROPANE AND HEAVIER HYDROCARBONS FROM A NATURAL GAS STREAM

[75] Inventor: Fred P. Apffel, Houston, Tex.

[73] Assignee: Flexivol, Inc., Houston, Tex.

[21] Appl. No.: 598,051

[22] Filed: Apr. 9, 1984

Related U.S. Application Data

[62] Division of Ser. No. 356,918, Mar. 10, 1982, Pat. No. 4,456,460.

[51] Int. Cl.$^4$ ................................................. F25J 3/02
[52] U.S. Cl. .......................................... 62/26; 62/28; 62/30; 62/31; 62/34; 62/40
[58] Field of Search ..................... 62/26, 9, 11, 23, 24, 62/27, 28, 29, 30, 31, 32–34, 42, 44, 40, 25

[56] References Cited

U.S. PATENT DOCUMENTS

| | | | |
|---|---|---|---|
| 3,592,015 | 7/1971 | Streich et al. | 62/40 |
| 3,596,472 | 8/1971 | Streich | 62/40 |
| 4,274,850 | 6/1981 | Becker | 62/38 |

Primary Examiner—Frank Sever
Attorney, Agent, or Firm—David M. Ostfeld

[57] ABSTRACT

A process and apparatus for economically recovering ethane, propane and heavier hydrocarbon components from methane and lighter constituents of natural gas streams is disclosed. The separation process of the natural gas stream is accomplished in two stages. The input gas stream (90) is first cooled by exchanger (58) using various streams of refrigerant. After cooling the stream (102) is partially condensed in a separator (104), with part of the methane and almost all of the ethane and heavier hydrocarbons within the stream being condensed. The condensed mixtures (112) are fed to a fractionation tower (116), where the methane and lighter gases are distilled from the other hydrocarbons. The cooling and condensation of the hydrocarbons in the feed stream and the heat source for the tower (116) are accomplished in indirect contact heat exchangers (26, 58, 68, 70) with a refrigerant. The cooling of the feed stream is also accomplished by flashing of the process gases. The refrigerant utilizes a mixture of hydrocarbons with the refrigerant process comprising compression, condensation, expansion and evaporation.

2 Claims, 3 Drawing Figures

PROCESS FOR RECOVERING ETHANE, PROPANE AND HEAVIER HYDROCARBONS FROM A NATURAL GAS STREAM

This is a division of application Ser. No. 356,918, filed Mar. 10, 1982, now U.S. Pat. No. 4,456,460.

TECHNICAL FIELD

The invention relates generally to processes for economically recovering valuable hydrocarbons from a natural gas stream. More specifically, it relates to an economical refrigeration process for recovering ethane, propane and heavier hydrocarbons from a natural gas stream by indirect heat exchange.

BACKGROUND ART

Natural gas is obtained from underground reservoirs and pumped through pipelines to various industrial and commercial consumers. Much of the natural gas is utilized for heating purposes and, accordingly, requires a BTU content of only 900 to 1000 BTU per m.c.f. A natural gas composed mainly of methane is sufficient to achieve such heating values. However, much of the natural gas obtained from underground reservoirs is rich in other components, such as ethane, propane, pentane and butane, which are heavier than methane. These components are industrially valuable in many processes, and, accordingly, separation of them from the methane prior to burning of the natural gas is highly desirable. Separation is usually accomplished at cryogenic temperature with distillation to separate and return methane to the gas pipe line while retaining a significant percentage of the ethane and heavier components.

Many processes have been devised for the cryogenic separation of methane from heavier components in a natural gas stream and for cryogenic refrigeration. Among these are U.S. Pat. Nos. 4,072,485 to Becdelievre et al; 4,022,597 to Bacon; 3,929,438 to Harper; 3,808,826 to Harper et al; Re. 29,914 to Perret; Re. 30,085 to Perret; 3,418,819 to Grunberg et al; 3,763,658 to Gaumer, Jr. et al; 3,581,510 to Hughes; 4,140,504 to Campbell et al; 4,157,904 to Campbell et al; 4,171,964 to Campbell et al; 4,278,457 to Campbell et al; 3,932,154 to Coers et al; 3,914,949 to Maher et al; and 4,033,735 to Swenson.

Several of these patents, such as those to Campbell et al and Bacon, utilize a cooling mechanism by turbo expansion Several use a plurality of successive, staged, external, indirect heat exchangers and/or totally condensing refrigerant, such as Becdelievre, Harper, Harper et al, Gaumer et al, Hughes, Coers et al, and Grunberg et al. Others use multistage flash systems separating refrigerant at various levels of temperature and pressure which emulates a cascade system in a closed loop mixed refrigerant scheme, such as those to Perret. Several also use single or very limited component refrigerant composition, such as Maher et al. Others use various schemes for refrigeration such as Swenson.

None of this prior art shows the process of the present invention for producing the cryogenic temperatures required for separation.

It is an object of the present invention to teach a method of cryogenic separation that lowers overall fuel consumption or horsepower to produce the cryogenic temperatures required.

It is a further object of the present invention to teach a method of cryogenic separation that permits broad latitude of operation. In particular, the ability to adjust the refrigerant composition to match the cooling and condensing characteristics of the feed in the process permits a degree of freedom not available in other process schemes more rigidly fixed or restrained by equipment designed for a specific process. This feature permits the process to process feed gases having a broad range of compositions, from the so-called "lean" to "rich" levels, without suffering in recovery efficiency.

It is yet another object of the present invention to teach a method of cryogenic separation wherein the turn-down capability is essentially unlimited.

It is yet a further object of the present invention to teach a method of cryogenic separation wherein the reduction in ethane and heavier hydrocarbon recovery efficiency is not nearly as pronounced on increasing through-put as it is with other systems.

It is yet an additional object of the present invention to teach a method of cryogenic separation wherein the process is less susceptible to $CO_2$ freezing problems, accepting higher $CO_2$ concentrations, because the demethanizer operates at warmer levels of temperature, higher demethanizer pressure, and a greater liquid-to-vapor ratio being fed to the tower.

DISCLOSURE OF THE INVENTION

A process and apparatus for economically removing heavier components of a vapor stream from lighter components of a natural gas stream is disclosed. It uses a mixed refrigeration system using two phase flow for refrigeration to facilitate separation of methane and lighter constituents of the natural gas stream from the hydrocarbon components, such as ethane, propane and heavier gases. The separation process of the natural gas stream is accomplished in two stages. First, the inlet gas stream is cooled in exchange with refrigerant and residue gas and partially condensed. Second, the condensed mixture and the cooler vapo stream are fed to a fractionation tower, where the methane and lighter gases are separated from the other hydrocarbons using indirect heat exchange with the mixed refrigerant to provide the energy if for distillation.

Distillation occurs at temperatures at $-195°$ F. to $-75°$ F. and at pressures at 200 to 500 psia. For lean gases, a portion of the liquid bottoms of the demethanizer column are fed to the inlet stream of natural gas to facilitate cooling. The process uses, exclusively, an indirect refrigerant system to reduce the temperature of the feed gas stream to the desired cryogenic temperature. The refrigerant system is self contained, operating on the same basic principal as a freon or propane refrigerant and using a two stage compression scheme.

The process apparatus consist of equipment operating on the process and the refrigerant streams.

With regard to the process stream, two sets of apparatus are associated with it. The first is the cooling and condensing section and the second is the demethanizer column.

With regard to the refrigerant stream, there are four basic sets of equipment that operate on it. These are: (1) compressors; (2) bottom reboiler; (3) side reboiler; and (4) refrigerant/feed exchanger.

Alternately, the refrigerant may be broken into two parts, one part fed to the first stage at compression and the second stage fed to the second stage of compression.

BRIEF DESCRIPTION OF THE DRAWINGS

For a further understanding of the nature and objects of the present invention, reference is made to the following drawings in which like parts are given like reference numerals, and wherein.

BEST AND ALTERNATE MODES FOR CARRYING OUT THE INVENTION

A process and apparatus for economically removing heavier components of a vapor stream from lighter components is disclosed. It uses a refrigeration system to facilitate separation of methane and lighter constituents of a natural gas stream from the hydrocarbon components, such as ethane, propane and heavier gases The separation process of the natural gas stream is accomplished in two stages. First, the inlet gas stream is cooled in exchange with refrigerant and residue gas. After cooling, the inlet stream is partially condensed, with part of the methane and almost all of the ethane and heavier hydrocarbons forming the condensate stream. Second, the condensed mixture and the cooler vapor stream are fed to a fractionation tower, where the methane and lighter gases are separated from the other hydrocarbons.

The cooling and condensation of the hydrocarbons in the feed stream is accomplished in an indirect contact exchange process with a stream of residue and refrigerant in indirect contact heat exchangers. The cooling is also accomplished by flashing of the feed stream gases.

The refrigerant utilizes a mixture of hydrocarbons, with the refrigerant process consisting of compression, condensation, expansion, and evaporation. The process uses exclusively an indirect refrigerant system to reduce the temperature of the feed gas stream to the desired cryogenic temperature. The refrigerant system is self contained, operating on the same basic principal as a freon or propane refrigerant scheme. However, the refrigerant is made up of, preferably, a mixture of hydrocarbons which include methane, ethylene, propane, butanes, and pentane. The composition range of the components of the refrigerant is set out in Table 1 below.

TABLE I

| Refrigerant Composition Range | |
|---|---|
| | Mol % |
| Nitrogen | 0-5 |
| Methane | 10-50 |
| Ethane | 20-50 |
| Ethylene | |
| Propane | 15-20 |
| I—Butane | 0-15 |
| N Butane | 0-15 |
| I Pentane | 0-15 |

As noted in Table I, ethane could be used in place of ethylene, and nitrogen could also be used. The mixture may be adjusted to match the cooling and condensing characteristics of the feed gas being refrigerated and the cryogenic temperature requirements.

The process apparatus consist of equipment operating on the process and the refrigerant streams.

With regard to the process stream, two sets of apparatus are associated with it. The first is the cooling and condensing section and the second is the demethanizer column.

With regard to the refrigerant stream, there are four basic sets of equipment that operate on it. These are: (1) compressors; (2) bottom reboiler; (3) side reboiler; and (4) refrigerant/feed exchanger.

REFRIGERATION CYCLE

The process uses an indirect refrigerant system to reduce the feed-gas stream to the desired cryogenic temperature. The refrigerant is compressed, heat of compression removed, cooled and condensed, expanded across a valve, and evaporated as it transfers the cold energy to the feed-gas stream. The system may be compounded by a multipath scheme devised to improve its efficiency. Additionally, the cold or evaporating refrigerant provides part of the energy to condense and subcool the warm refrigerant to the desired temperature.

The refrigerant is made up of a mixture of hydrocarbons. These include, preferably, methane, ethylene, propane, butanes, and pentane described above. The concentration of these components may be adjusted to match the cooling and condensing characteristics of the feed gas being refrigerated and the cryogenic temperature requirement.

Figure 2:
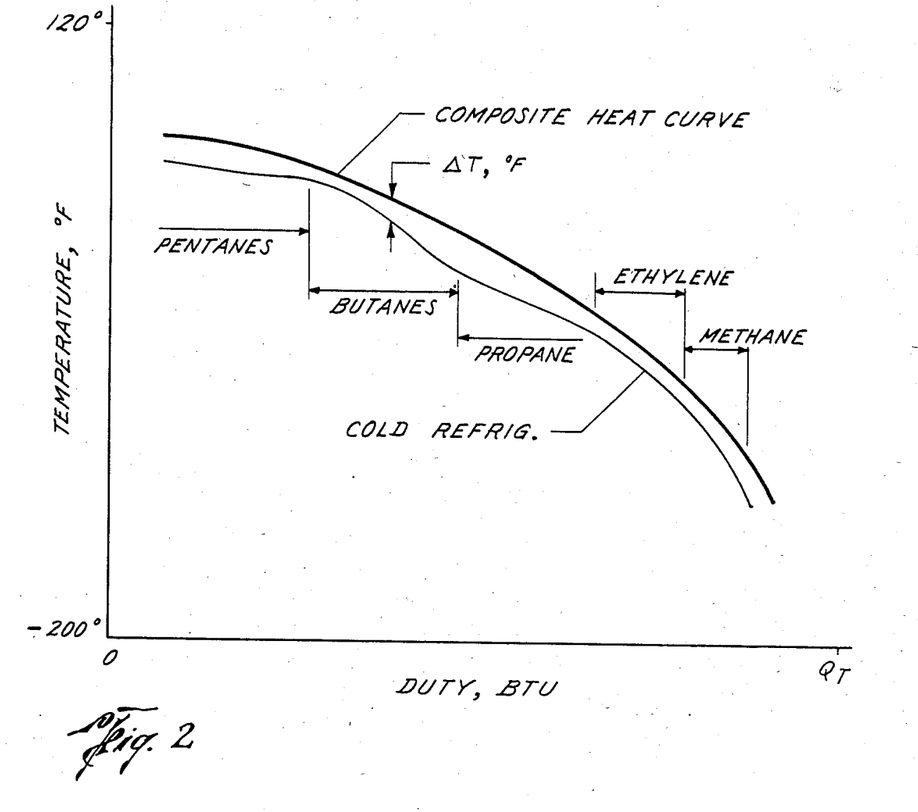
FIG. 2 is a heat-temperature relationship between the processed natural gas and the cold-producing fluid or refrigerating fluid.

The components are adjusted to minimize the area between the warm condensing and cold evaporating streams, as illustrated in FIG. 2. Additionally, the refrigerant flow rate and refrigerant compression ratio may be varied to further adjust the refrigerant system. Each of the variables is optimized to produce the most efficient, economic refrigerant design for the feed gas being processed.

The operation of the refrigerant system is fully automated and easy to control. However, the addition of refrigerant components is not automatic. To determine the addition of refrigerant components, a multipoint recorder may be provided, which produces equally spaced temperatures along the path of the warm and cold refrigerant streams in the Feed/Refrigerant Exchanger. A plot of this data will reveal the area where these curves are too close together, as well as the temperature level. If it occurs in the area where ethylene evaporates, for example, this refrigerant should then be added. Adding a couple of refrigerant bottles similar in size to an oxygen or acetylene bottle will normally correct any problem. The system is not overly sensitive to the refrigerant composition. A chromatograph may also be provided to determine the refrigerant composition from time to time. The operator can adjust the refrigerant accordingly.

Figure 1:
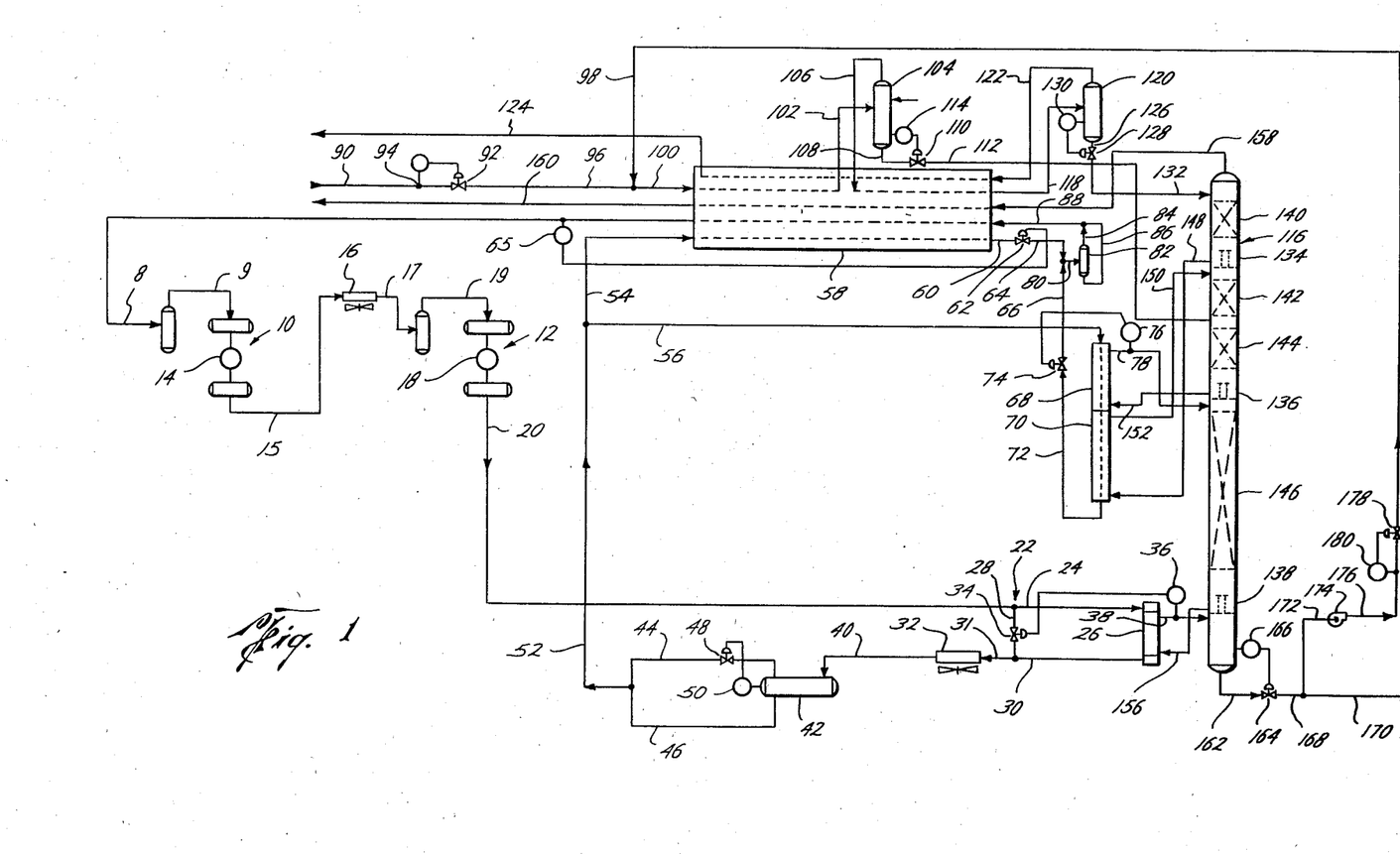
FIG. 1 is a flow diagram of a first, preferred embodiment of the present invention.

In the disclosed embodiments of the present invention, the refrigeration cycle includes introducing inlet stream 8 into two stages of compression 10, 12. Refrigerant in stream 8 is fed to the first stage 10 of compression. The composition range of the inlet stream 8 to the first compression stage 10 is set out in Table 1.

Each stage includes a refrigerant compressor suction scrubber, and a compressor. The sizes of the scrubbers depend upon the size of the refrigerant system. They are typically fabricated units and can be purchased from any number of vendors including Watts Company, McIver and Smith, and Taylor Tank. The compressors are preferably reciprocating compressors, such as that built by Ingersoll Rand Co., Worthington Corp. and Clark Industries. It is recognized that the compressors could also be a centrifugal but with overall lower horsepower efficiency.

The first stage 10 of compression includes compressor 14. Compressor 14 should be sized to raise the stream pressure from an inlet pressure of 20-100 psia to a discharge pressure in stream 15 of 100-250 psia for an inlet temperature range of 80°– 120° F. and an outlet temperature range of 180°-200° F. The discharge 15 from the first compression stage 14 enters first stage refrigerant compressor after cooler 16. The outlet of after cooler 16 enters the second stage 12 of compression.

Second stage 12 of compression includes second stage compressor 18. The second stage compressor 18 should be sized to raise the inlet 15 pressure from 100-250 psia to a pressure at the outlet 20 of 250-600 psia with a temperature rise from the inlet 17 from after cooler 16 of 80°-120° F. to an outlet 20 temperature of 250°-380° F.

Those skilled in the art will recognize that there are several methods of obtaining adequate compression of refrigerant gases in a two stage process. The present invention should not be limited to any particular physical design of the two stage refrigerant system. The alternative examples given above are given merely as illustration and are not intended to limit the scope of this invention.

The outlet stream 20 of compressor second stage 12 enters the demethenizer bottom system 22. Demethanizer bottom system 22 includes a split stream system having a first stream 24 flowing to reboiler 26 and a second stream 28 which by-passes reboiler 26. The effluent 30 from reboiler 26 rejoins by-pass stream 28 to form stream 31 which is fed to the second stage refrigerant compressor after cooler 32. The refrigerant, hot in stream 20 from the adiabatic heat of compression, is used for heat in the demethanizer bottoms reboiler 26. Stream 31 is further cooled with air or water by cooler 32 to the lowest reasonable temperature that can be obtained. For an air cooler, this is normally 120° to 130° F. With cooling water, this temperature is normally 60° to 90° F.

The flow in stream 24 to the demethanizer reboiler 26 and the flow to the by-pass stream 28 is selectively controlled by temperature control valve 34. The temperature control valve 34, responsive to temperature sensor/controller 36, opens allowing more refrigerant flow to the demethanizer bottoms reboiler 26 as the demethanizer bottoms reboiler effluent 38 temperature drops below the set point of 120° to 150° F. or closes reducing the flow if the demethanizer bottoms reboiler effluent 38 temperature rises above the set point.

The refrigerant stream 40 at a temperature of 60° to 130° F. and pressure of 250 to 600 psia from the second stage after cooler 32 then enters the second stage compressor discharge scrubber 42. This unit acts as surge capacity for the system.

The vapor and liquid are separated in scrubber 42. The vapor and liquid streams exit separately from scrubber 42 as two effluent streams, vapor stream 44 and liquid stream 46. The amount of vapor in stream 44 is controlled by valve 48. This valve 48 opens and closes in response to the level in scrubber 42 sensed by level sensor/controller 50. The liquid is forced from the separator by the use of valve 48. The vapor stream 44 and liquid stream 46 are subsequently recombined to form a two phase refrigerant stream 52. Stream 52 is then split into two streams 54, 56. Stream 54 is fed to heat exchanger 58.

Heat exchanger 58 is a multi-path process stream heat exchanger for use in exchanging energy between warm process and refrigerant streams and cold process and refrigerant streams. Exchanger 58 is, preferably, the brazed aluminum type as manufactured by the Trane Company. The passages are approximately ⅜ inches deep by 3 to 4 feet wide by 12 to 20 feet long. The width, length and number of passages depends on the quantity of energy being transferred and flow requirement of the process and refrigerant streams, both warm and cold. The flow of the warm and cold streams is countercurrent in each passage. The distribution of these streams is accomplished with manifolds across the depth of the passages. Those passages selected for the stream to flow through are open; the others are blocked. The selection of the stream flow paths is strategically selected to optimize heat transfer efficiency.

Refrigerant stream 54 is fed to exchanger 58 where it is condensed and subcooled to the same temperature of the feed gas to the exchanger, −80° to −220° F., and exits as stream 60. The pressure of stream 60 is lowered substantially as the refrigerant expends across Joule - Thompson control valve 62, thus producing temperatures from 5° F. to 40° F. colder. Valve 62 is controlled by pressure sensor/controller 65 in stream 8. Valve 62 prevents the flow of fluid to stream 64 whenever pressure in stream 6 is above a predetermined set point. The outlet stream 64 of valve 62 is recombined with stream 66 from the side reboilers.

Stream 66 originates from split stream 56. Split stream 56 is used to heat the demethanizer side reboilers 68, 70. The refrigerant flows from stream 66 through side reboilers 68, 70 and exists the reboilers in stream 72 with a temperature of −80° to −150° F. The pressure of stream 72 is lowered substantially as the refrigerant expands across Joule—Thompson control valve 74, thus producing temperatures from 5° F. to 40° F. colder. Valve 74 is controlled by temperature sensor/controller 76 in side stream 78. Valve 74 constrains the flow of fluid to stream 66 whenever the side reboiler stream 78 temperature rises above the set point, and permits greater fluid flow to stream 66 whenever the side reboiler stream 78 temperature falls below the set point.

Streams 64 and 66 are recombined into stream 80 which flows into cold refrigerant separator 82. The vapor and liquid are separated in separator 80. The vapor and liquid streams exit separately as two effluent streams, vapor stream 84 and liquid stream 86. Vapor stream 84 and liquid stream 86 are subsequently recombined to form a two phase refrigerant stream 88 with a temperature of −90° F. to 220° F. Stream 88 re-enters exchanger 58. Stream 88 provides part of the refrigerant energy to the streams being cooled and condensed, such as the feed gas and warm refrigerant streams, as it evaporates. This refrigerant exits exchanger 58 in stream 8 to return to the suction of the first compressor stage 10.

PROCESS STEAM

As shown in FIG. 1, process inlet or feed gas enters the process at stream 90. The amount of gas entering the process is controlled by valve 92. Valve 92 increases its opening if the flow measured by sensor/controller 94 is lower than a predetermined set point, and decreases it opening if the flow measured by sensor/controller 94 is higher than a predetermined set point. The gas exits valve 92 in stream 96.

The typical feed gas composition range is set out in the following Table II:

TABLE II

FEED GAS RANGE OF COMPOSITION

| COMPONENT | RICH GAS MOL % | LEAN GAS MOL % |
|---|---|---|
| NITROGEN | 3.74 | .24 |
| CARBON DIOXIDE | .70 | .36 |
| METHANE | 75.52 | 92.00 |
| ETHANE | 11.60 | 4.52 |
| PROPANE | 5.05 | 1.97 |
| I—BUTANE | .63 | .24 |
| N—BUTANE | 1.48 | .31 |
| I—PENTANE | .37 | .11 |
| HEXANE | .27 | .17 |
| HEPTANE | .30 | .00 |
| TOTAL | 100.00 | 100.00 |

The pressure range of the inlet gas is 15 to 1500 psia, with a temperature range of 50° to 150° F.

After the process inlet gas enters the process, it is dehydrated prior to entering exchanger 58.

Dehydration, or removal of any moisture that the inlet gas may contain, is imperative. Even slight amounts of water in the gas stream at the cryogenic temperatures required to separate the methane from the heavier hydrocarbons will form hydrates and freeze. This will subsequently plug up the equipment and piping.

The dehydration is accomplished by processing the gas through a vessel, not shown, containing, for example, molecular sieve material. The molecular sieve material is porous and water, being a smaller molecule than the hydrocarbons, is preferentially adsorbed into its pores. The gas exits the dehydration unit essentially free of moisture. The molecular sieve bed becomes saturated with water after a period of time and has to be regenerated. Therefore, two adsorption vessels are required. One is always in adsorption service while the other is being regenerated.

The regeneration is achieved by recycling a slip stream of the dry residue gas. Approximately 8 to 10 percent of the through-put gas is required for this purpose. The regeneration gas is compressed and heated to approximately 550° F. and processed through the dehydrator being regenerated, driving the moisture from the molecular sieve. This hot regeneration gas bearing the desorbed moisture is subsequently cooled, and the major part of the water is condensed from the gas. The water is dumped to the process sewer, and the regeneration gas is recycled to the main residue-gas stream. After the water has been removed from the molecular sieve, the heater is bypassed or turned off, and the dehydrator is cooled to ambient or inletgas temperature, using the regeneration gas.

The adsorption cycle is generally set for this type of plant at eight hours; the heating cycle at three hours; and the cooling cycle at two hours.

The stream 96 is then joined by recycle stream 98 of heavier hydrocarbons to form stream 100. The mixture in stream 100 is fed directly to the feed-refrigerant exchanger 58.

The amount of material in recycle stream 98 is determined by the feed-gas composition. The so-called lean feed-gas streams, wherein the composition of a single component approaches 100%, see Table II, tend to condense at a single temperature. Matching a fixed refrigerant to this is possible, but the energy composition increases proportionally. Recycling part of the heavier hydrocarbon compounds distributes the condensation over a wider range and then subsequently reduces the energy consumption and exchanger service requirements.

Feed stream 100 is cooled in exchanger 58, and part of the heavier hydrocarbons are condensed. Depending on feed gas composition and pressure, the feed gas is cooled to an intermediate temperature level ranging from −10° F. to −60° F. At this point a large part of the heavier hydrocarbons is condensed. This cooled and partially condensed stream is withdrawn from exchanger 58 in stream 102 which is fed to feed gas separator 104. The vapor and liquid are separated in separator 104. The vapors return to the exchanger 58 via stream 106, where they are further cooled, and where additional condensation of heavier hydrocarbons takes place. The condensed liquid from the first feed-gas separator 104 exits via stream 108 which is controlled by valve 110. The liquid exits valve 110 in stream 112. To prevent gas from entering stream 108, a liquid level is maintained in the feed-gas separator 104, using level control sensor/controller 114 and level control valve 110.

Stream 112 is connected to demethanizer 116 at a point where the liquid in stream 112 entering the tower 116 matches approximately the temperature profile of the tower 116 at that point as nearly as possible. Removing the heavier hydrocarbons reduces the refrigerant energy requirements. This feature is not necessary when processing very lean gases.

The vapor in stream 106, which enters the refrigerant/feed exchanger 58, leaves the exchanger 58 at temperatures of −80° F. to −220° F. via stream 118. Stream 118 may be fed directly to the top of demethanizer 116, when the feed-gas pressure is 550 psia or less. When the feed-gas pressure is greater than 550 psia, such as 700 psia, stream 118 is fed to a second feed-gas separator 120 via stream 118, as is shown in FIG. 1, where the liquid and vapor in the stream 118 are separated. Separating the vapor and liquid at the higher pressure reduces the recompression energy consumption. The vapor is recycled through stream 122 to refrigerant/feed gas exchanger 58. Refrigerant energy is recovered from the vapor in stream 122 as it flows countercurrent to the incoming feed. The vapor exits heat exchanger 58 via stream 124 where it leaves the battery limits of the plant.

The liquid from the second feed-gas separator 120 is fed via stream 126 to level control valve 128. The liquid level in the second feed-gas separator 120 is controlled by the level control instrument sensor 130 manipulating valve 128. Flow from level control valve 128 to the demethanizer 116 occurs via stream 132. Stream 132 is connected to the dementhanizer 116 at a point where the liquid in stream 132 matches approximately the temperature profile at the tower 116 at that point as nearly as possible.

Demethanizer 116 should preferably operate at pressures below 550 psia to accomplish the separation of methane from heavier components. Therefore, where feed gases are cooled and condensed above this pressure level, the level control valves 110, 128 act as expansion valves as well as level control valves. In this way, the pressure is lower to that of demethanizer 116.

The use of an external or indirect refrigerant system permits the demethanizer 116 to operate at much higher pressures. The upper process pressure range for the demethanizer 116 is usually limited to the range of 500 to 550 psia. Operating the dementhanizer at this level of pressure reduces the limits of temperature to which the feed gas must be cooled. At these pressures, a temperature of −80° to −120° F. is all that is required to liquify sufficient ethane to meet or exceed most ethane-recovery requirements.

The demethanizer 116 is designed with side reboilers 68, 70 and bottom reboilers 26, all of which are indirect heat exchangers. The side reboilers 68, 70 are usually located on the dementhanizer 116 to permit the maximum recovery of cryogenic energy and to provide a more uniform distribution of vapor-liquid traffic. This reduces the tower size, and recovery of the cryogenic energy lowers the refrigerant horsepower requirements. These reboilers may be connected as one unit or separated and the number of side reboilers should not be considered a limitation of the invention. When the side reboilers 68, 70 are connected into one reboiler, the refrigerant discharge of side reboiler 68 is directly connected to the refrigerant inlet of side reboiler 70.

Demethanizer column 116 preferably has three chimney trays 134, 136 and 138 separated by packings 140, 142, 144 and 146. Typically, inlet stream 112 enters demethanizer 176 between packing 142 and packing 144. Inlet stream 132 enters the demethanizer above packing 140.

The process inlet of side reboiler 70 comes from liquid entrapped in chimney tray 134 through stream 148 and re-enters demethanizer column 116 between packer 142 and tray 134 by stream 150. The inlet to side reboiler 68 enters from tray 136 through stream 152 and re-enters the demethanizer 16 between packing 146 and tray 134 by reboiler discharge stream 78. In the preferred embodiment, the process streams flow counter/-current with the refrigerant stream 56.

The bottom tray 138 of demethanizer 116 is connected to bottom reboiler 26. The connection is made by an inlet process stream 156 connecting reboiler 26 to tray 138. The discharge from reboiler 26 is connected to the demethanizer 116 by process stream 38 to the section of demethanizer 116 below chimney tray 138. In the preferred embodiment, refrigerant stream 24 flows countercurrent with the process stream 156.

Demethanizer 116 may be obtained from several companies, such as Taylor Tank, Inc., McIver, and Smith Industries. The materials of construction of demethanizer 116 are, for example, 304 stainless steel, and it trays 134, 136, 138 may also be of 304 stainless steel. The packings 140, 142, 144, 146 may be, for example, pall rings made of aluminum. The trays and packings may be obtained from several companies, such as Glitch, Inc. and Kock Engineering.

Reboilers 26, 68, 70 may be, for example, the fixed tube sheet, vertical, once-through shell and tube carbon steel exchangers, such as those manufactured by Kruger Engineering and Manufacturing Company and The Dowan Corporation.

The vapor outlet of demethanizer 116 is connected to heat exchanger 58 by stream 158. Stream 158 has a temperature of −195° to −75° F. and a pressure of 200 to 550 psia. Refrigerant energy is recovered from the vapor in stream 158 as it flows countercurrent to the incoming feed. The vapor exits heat exchanger 58 via stream 160 with a temperature of 50° to 110° F. and a pressure of 100 to 500 psia where it leaves the battery limits of the plant.

The bottom of demethanizer 116 is connected to outlet stream 162 which has a temperature of 30° to 120° F. and a pressure of 200 to 550 psia and which is the inlet of level control valve 164. Valve 164 moves towards its closed position, lowering the flow rate through stream 162 if the level, measured by level sensor/controller 166 in demethanizer 116 bottoms falls below a predetermined set point and opens, raising the flow rate, if the level rises above the set point.

The refrigeration process is an integral part of the distillation or fractionation process, providing heat energy while recovering refrigeration energy at the same time.

The distillation is accomplished by applying heat energy appropriately along the length of the distillation tower 116, while at the same time recovering refrigerant energy. The heat energy at the base of the demethanizer 116 is from the refrigerant in stream 24 entering bottom reboiler 26 and flowing countercurrent to the liquid trapped on the lower chimney tray 138 that flows to the bottom reboiler 26 in stream 156 and exits in conduit 38. The material in stream 38 has two phases, vapor and liquid. The vapor flows up the tower 116; liquid exits the tower via conduit 162. A level is maintained in the bottom of demethanizer 116 using the level controller 166, which operates, level-control valve 164.

Additional heat energy is provided to the distillation tower 116 from the side reboilers 68, 70. Liquid is trapped at an intermediate level in demethanizer 116 in chimney tray 136 and fed via conduit 152 to side reboiler 68. It exits this reboiler 68 via conduit 78, returning, partially vaporized, to demethanizer 116. Similarly, heat is added, and refrigerant energy recovered, at a higher level, in the demethanizer 116. Liquid trapped in chimney tray 134 flows via conduit 148 to reboiler 70 and exits reboiler 70 in conduit 158 to return to demethanizer 116. The exiting liquid in conduit 158 is partially vaporized and introduced into demethanizer 116.

The outlet stream 168 of level valve 164 splits into two streams 170, 172. Stream 170 conveys ethane and heavier hydrocarbons out of the battery limits of the plant. Stream 172 is the inlet stream to pump 174. The discharge of pump 174, stream 176, is connected to the inlet of flow valve 178. The discharge of flow valve 178 is connected to stream 98 which joins stream 96 to form the inlet stream 100 to exchanger 58. Valve 178 moves to raise and lower flow rate in response to the flow rate measured by flow sensor/controller 180 in comparison to a predetermined set point.

As discussed earlier, the incoming feed-gas composition may be very high in one component, approaching that of a single component such as methane; i.e. exceeding 90 mole percent. In such an instance, more refrigerant energy is required to condense the ethane in heavier hydrocarbons because the condensation occurs over a very narrow temperature range and at a much lower temperature. To reduce or eliminate this problem, part of the stream containing heavier hydrocarbons may be recycled in such an event. This may amount to approximately 20 to 40% of the product flow rate. Such recycling is achieved in stream 98. Pump 174 pumps the fluid pressure up to that of the inlet pressure at stream 96.

EXAMPLE

The following is given as an example that illustrates, but should not limit, the present invention. The example is given in the form of Tables III and IV which shows steady state process and refrigerant flows and theoretical tray flows respectively, and where the stream numbers correspond to the stream numbers of FIG. 1. The use of "V" and "L" before a stream number denotes the vapor and liquid phase of the stream respectively. The number "2" before a stream number denotes a two phase stream of liquid and vapor.

TABLE III

| COMP | M.W. | G/MOL | 90 (2) | 96 (2) | 100 (2) | 102 (2) | 106 (V) | STREAM 108 (L) | 112 (2) | V112 (V) | L112 (L) | 118 (2) | 158 (V) | 160 (V) | 150 (2) |
|---|---|---|---|---|---|---|---|---|---|---|---|---|---|---|---|
| | | | | | | | | FLOW RATES LBMOL/HR (PHASE) | | | | | | | |
| N2 | 28.02 | 4.17 | 71.70 | 61.70 | 61.70 | 61.70 | 58.04 | 3.66 | 3.66 | 2.62 | 1.03 | 58.04 | 20.50 | 20.50 | .40 |
| CO2 | 44.01 | 6.40 | 11.60 | 11.60 | 11.60 | 11.60 | 8.19 | 3.41 | 3.41 | .61 | 2.81 | 8.19 | 5.03 | 5.03 | 12.77 |
| CH4 | 16.04 | 6.42 | 1246.00 | 1246.00 | 1246.00 | 1246.00 | 1052.28 | 193.72 | 193.72 | 75.04 | 118.68 | 1052.28 | 653.62 | 653.62 | 118.10 |
| C2H6 | 30.07 | 9.56 | 191.40 | 191.40 | 191.40 | 191.40 | 97.54 | 93.86 | 93.86 | 6.39 | 87.47 | 97.54 | 21.73 | 21.73 | 111.30 |
| C3H8 | 44.09 | 10.45 | 83.30 | 83.30 | 83.30 | 83.30 | 19.69 | 63.61 | 63.61 | .94 | 62.67 | 19.69 | .97 | .97 | 18.36 |
| IC4H10 | 58.12 | 12.41 | 10.40 | 10.40 | 10.40 | 10.40 | 1.21 | 9.19 | 9.19 | .04 | 9.15 | 1.21 | .02 | .02 | 1.13 |
| NC4H10 | 58.12 | 11.95 | 24.40 | 24.40 | 24.40 | 24.40 | 2.07 | 22.33 | 22.33 | .07 | 22.26 | 2.07 | .02 | .02 | 1.95 |
| IC5H12 | 72.15 | 13.88 | 6.10 | 6.10 | 6.10 | 6.10 | .23 | 5.87 | 5.87 | .01 | 5.87 | .23 | .00 | .0 | .22 |
| NC5H12 | 72.15 | 13.74 | 5.60 | 5.60 | 5.60 | 5.60 | .16 | 5.44 | 5.44 | .00 | 5.44 | .16 | .00 | .0 | .15 |
| NC6H14 | 86.17 | 15.56 | 4.50 | 4.50 | 4.50 | 4.50 | .04 | 4.46 | 4.46 | .00 | 4.46 | .04 | .00 | .0 | .04 |
| NC7H16 | 100.20 | 17.49 | 5.00 | 5.00 | 5.00 | 5.00 | .01 | 4.99 | 4.99 | .00 | 4.99 | .01 | .00 | .0 | .01 |
| TOTAL | | | 1650.00 | 1650.00 | 1650.00 | 1650.00 | 1239.45 | 410.55 | 410.55 | 85.72 | 324.83 | 1239.45 | 701.89 | 701.89 | 264.42 |
| TEMPERATURE DEG F | | | 100.0 | 100.0 | 100.0 | −40.0 | −40.0 | −40.0 | −59.1 | −59.1 | −59.1 | −92.0 | −111.4 | 100.0 | −55.0 |
| PRESSURE PSIA | | | 800.0 | 800.0 | 800.0 | 795.0 | 795.0 | 795.0 | 503.0 | 503.0 | 503.0 | 790.0 | 500.0 | 495.0 | 501.0 |
| TOTAL ENTHAL MMBTU/HR | | | 7.050 | 7.050 | 7.050 | 2.604 | 3.070 | −.466 | −.466 | .266 | −.693 | 1.149 | 1.427 | 3.014 | −.123 |
| SPECF ENTHAL BTU/LB | | | 199.08 | 199.08 | 199.08 | 73.54 | 134.13 | −37.25 | −37.25 | 146.40 | −63.11 | 50.19 | 119.09 | 251.56 | −18.06 |
| PSEUDO TC DEG F | | | −63.4 | −63.4 | −63.4 | −63.4 | −97.9 | 40.6 | 40.6 | −99.0 | 77.5 | 97.9 | −111.5 | −111.5 | 8.3 |
| PSEUDO PC PSIA | | | 665.1 | 665.1 | 665.1 | 665.1 | 668.9 | 653.7 | 653.7 | 672.3 | 648.8 | 668.9 | 671.7 | 671.7 | 701.8 |
| PSEUDO TR | | | 1.412 | 1.412 | 1.412 | 1.412 | 1.160 | .839 | .801 | 1.111 | .746 | 1.016 | 1.000 | 1.608 | .865 |
| PSEUDO PR | | | 1.203 | 1.203 | 1.203 | 1.195 | 1.189 | 1.216 | .769 | .748 | .775 | 1.181 | .744 | .737 | .714 |
| PSEUDO ACENT | | | .033 | .033 | .033 | .033 | .018 | .078 | .078 | .017 | .095 | .018 | .011 | .011 | .066 |
| LVOL/MOL @ 60 F GAL/MOL | | | 0.00 | 0.00 | 0.00 | 0.00 | 0.00 | 8.61 | 0.00 | 0.00 | 9.14 | 0.00 | 0.00 | 0.00 | 0.00 |
| STP GAS VOL MMSCFD | | | 0.000 | 0.000 | 0.000 | 0.000 | 11.324 | 0.000 | 0.000 | .783 | 0.000 | 0.000 | 1.427 | 6.413 | 0.000 |
| DENSITY @ T,P LB/CUFT | | | 0.0000 | 0.0000 | 0.0000 | 0.0000 | 11.8191 | 28.2659 | 0.0000 | 7.3268 | 29.2387 | 0.0000 | 4.4528 | 2.7434 | 0.0000 |
| SPEC GRAV | | | 0.0000 | 0.0000 | 0.0000 | 0.0000 | .6375 | .4246 | 0.0000 | .6221 | .4436 | 0.0000 | .5891 | .5891 | 0.0000 |
| LV/MIN @ 60 F GAL/MIN | | | 0.00 | 0.00 | 0.00 | 0.00 | 0.00 | 58.94 | 0.00 | 0.00 | 46.80 | 0.00 | 0.00 | 0.00 | 0.00 |
| LV/MIN @ T,P GAL/MIN | | | 0.00 | 0.00 | 0.00 | 0.00 | 0.00 | 55.23 | 0.00 | 0.00 | 46.80 | 0.00 | 0.00 | 0.00 | 0.00 |
| GVOL/MIN @ T,P CUFT/MIN | | | 0.00 | 0.00 | 0.00 | 0.00 | 32.28 | 0.00 | 0.00 | 3.51 | 0.00 | 0.00 | 44.84 | 72.78 | 0.00 |
| Z(SRK) | | | 0.0000 | 0.0000 | 0.0000 | 0.0000 | .2758 | .2026 | 0.0000 | .2878 | .2112 | 0.0000 | .5126 | .5126 | 0.0000 |
| MASS LB | | | 35410.9 | 35410.9 | 35410.9 | 35410.9 | 22891.2 | 12519.7 | 12519.7 | 1545.0 | 10974.7 | 22891.2 | 11979.5 | 11979.5 | 6833.4 |
| MOL WT LB/LBMOL | | | 21.461 | 21.461 | 21.461 | 21.461 | 18.469 | 30.495 | 30.495 | 18.023 | 33.786 | 18.469 | 17.068 | 17.068 | 25.843 |

| COMP | M.W. | G/MOL | 148 (L) | 152 (L) | 78 (2) | 156 (L) | 38 (2) | STREAM 162 (L) | 170 (L) | 122 (V) | 126 (L) | 132 (2) | V132 (V) | L132 (L) | 124 (V) |
|---|---|---|---|---|---|---|---|---|---|---|---|---|---|---|---|
| | | | | | | | | FLOW RATES LBMOL/HR (PHASE) | | | | | | | |
| N2 | 28.02 | 4.17 | .40 | .08 | .08 | .00 | .00 | 0.00 | 0.00 | 40.13 | 17.91 | 17.95 | 12.31 | 5.64 | 40.13 |
| CO2 | 44.01 | 6.40 | 12.77 | 19.28 | 19.28 | 11.41 | 11.41 | 3.45 | 3.45 | 3.28 | 4.91 | 4.91 | .83 | 4.09 | 3.28 |
| CH4 | 16.04 | 6.42 | 118.10 | 101.10 | 101.10 | 16.62 | 16.62 | 3.54 | 3.54 | 572.19 | 480.09 | 480.85 | 188.15 | 292.70 | 572.19 |
| C2H6 | 30.07 | 9.56 | 111.30 | 298.30 | 298.30 | 337.10 | 337.10 | 141.60 | 141.60 | 27.42 | 70.12 | 70.17 | 4.79 | 65.37 | 27.42 |
| C3H8 | 44.09 | 10.45 | 18.36 | 99.83 | 99.83 | 132.10 | 132.10 | 79.50 | 79.50 | 2.82 | 16.87 | 16.87 | .23 | 16.64 | 2.82 |
| IC4H10 | 58.12 | 12.41 | 1.13 | 11.43 | 11.43 | 14.25 | 14.25 | 10.28 | 10.28 | .10 | 1.11 | 1.11 | .01 | 1.10 | .10 |
| NC4H10 | 58.12 | 11.95 | 1.95 | 26.27 | 26.27 | 31.94 | 31.94 | 24.20 | 24.20 | .14 | 1.93 | 1.93 | .01 | 1.93 | .14 |
| IC5H12 | 72.15 | 13.88 | .22 | 6.32 | 6.32 | 7.20 | 7.20 | 6.09 | 6.09 | .01 | .22 | .22 | .00 | .22 | .01 |
| NC5H12 | 72.15 | 13.74 | .15 | 5.77 | 5.77 | 6.47 | 6.47 | 5.60 | 5.60 | .00 | .15 | .15 | .00 | .15 | .00 |
| NC6H14 | 86.17 | 15.56 | .04 | 4.55 | 4.55 | 6.47 | 6.47 | 4.50 | 4.50 | .00 | .04 | .04 | .00 | .04 | .00 |
| NC7H16 | 100.20 | 17.49 | .01 | 5.02 | 5.02 | 5.20 | 5.20 | 5.00 | 5.00 | .00 | .01 | .01 | .00 | .01 | .00 |

TABLE III-continued

| | | | | | | | | | | | |
|---|---|---|---|---|---|---|---|---|---|---|---|
| TOTAL | 264.42 | 577.96 | 577.96 | 568.75 | 568.75 | 283.75 | 283.75 | 646.08 | 593.37 | 594.22 | 206.33 | 387.90 | 646.08 |
| TEMPERATURE DEG F | −73.0 | 11.0 | 39.0 | 88.4 | 116.9 | 116.0 | 116.0 | −92.0 | −92.0 | −118.8 | −118.8 | −118.8 | 100.0 |
| PRESSURE PSIA | 501.0 | 503.0 | 503.5 | 505.0 | 505.0 | 505.0 | 505.0 | 790.0 | 790.0 | 500.0 | 500.0 | 500.0 | 785.0 |
| TOTAL ENTHAL MMBTU/HR | −.323 | −.512 | .153 | .354 | 1.693 | .334 | .334 | 1.063 | .086 | .089 | .403 | −.314 | 2.683 |
| SPECF ENTHAL BTU/LB | −47.21 | −25.87 | 7.73 | 16.47 | 78.82 | 28.54 | 28.54 | 93.16 | 7.49 | 7.74 | 113.44 | −39.58 | 235.13 |
| PSEUDO TC DEG F | 8.3 | 100.0 | 100.0 | 142.8 | 142.8 | 170.3 | 170.3 | −112.3 | −82.2 | −82.2 | −117.4 | −63.5 | −112.3 |
| PSEUDO PC PSIA | 701.8 | 679.1 | 679.1 | 669.8 | 669.8 | 648.8 | 648.8 | 665.2 | 672.9 | 672.9 | 664.7 | 677.2 | 665.2 |
| PSEUDO TR | .826 | .841 | .891 | .910 | .957 | .914 | .914 | 1.058 | .974 | .903 | .996 | .961 | 1.611 |
| PSEUDO PR | .714 | .741 | .741 | .754 | .754 | .778 | .778 | 1.188 | 1.174 | .743 | .752 | .738 | 1.180 |
| PSEUDO ACENT | .066 | .106 | .106 | .123 | .123 | .136 | .136 | .013 | .024 | .024 | .011 | .031 | .013 |
| LVOL/MOL @ 60 F GAL/MOL | 8.10 | 9.43 | 0.00 | 10.06 | 0.00 | 10.45 | 10.45 | 0.00 | 6.87 | 0.000 | 1.885 | 7.14 | 0.00 |
| STP GAS VOL MMSCFD | 0.000 | 0.000 | 0.000 | 0.000 | 0.000 | 0.000 | 0.000 | 5.903 | 0.000 | 0.0000 | 0.000 | 0.000 | 5.903 |
| DENSITY @ T,P LB/CUFT | 25.7286 | 28.0264 | 28.2135 | 28.2135 | 0.0000 | 29.4459 | 29.4459 | 6.8978 | 24.0222 | 0.0000 | 2.5278 | 24.2262 | 2.4908 |
| SPEC GRAV | .3829 | .4358 | .4502 | .4502 | 0.0000 | .4736 | .4736 | .6097 | .3378 | .0000 | .5947 | .3439 | .6097 |
| LVOL/MIN @ 60 F GAL/MIN | 35.68 | 90.83 | 95.38 | 95.38 | 0.00 | 49.42 | 49.42 | 0.00 | 67.95 | 0.00 | 0.00 | 46.16 | 0.00 |
| LVOL/MIN @ T,P GAL/MIN | 33.12 | 88.10 | 94.92 | 94.92 | 0.00 | 49.57 | 49.57 | 0.00 | 59.59 | 0.00 | 0.00 | 40.87 | 0.00 |
| GVOL/MIN @ t,P CUFT/MIN | 0.00 | 0.00 | 0.00 | 0.00 | 595.44 | 0.00 | 0.00 | 27.57 | 0.00 | 0.0000 | 23.44 | 0.00 | 76.35 |
| Z(SRK) | .7581 | .1303 | .1276 | .1276 | .7763 | .2317 | .2317 | .5126 | .2212 | .0000 | .9314 | .8696 | .9266 |
| MASS LB | 6833.4 | 19803.0 | 19803.0 | 21477.8 | 21477.8 | 11707.3 | 11707.3 | 11411.0 | 11480.5 | 11495.3 | 3554.7 | 7940.6 | 11411.0 |
| MOL WT LB/LBMOL | 25.843 | 34.264 | 34.264 | 37.763 | 37.763 | 41.259 | 41.259 | 17.662 | 19.347 | 19.345 | 17.229 | 20.471 | 17.662 |

STREAM

| COMP | M.W. | G/MOL | 8 | 9 | 15 | 17 | 19 | 20 | 24 | 30 | 31 | 40 | 64 | 46 |
|---|---|---|---|---|---|---|---|---|---|---|---|---|---|---|
| | | | (V) | (V) | (V) | (V) | (V) | (V) | (V) | (2) | (2) | (2) | (2) | (L) |
| CH4 | 16.04 | 6.42 | 205.20 | 205.20 | 205.20 | 205.20 | 205.20 | 205.20 | 205.20 | 205.20 | 205.20 | 205.20 | 182.02 | 13.51 |
| C2H4 | 28.05 | 9.66 | 345.60 | 345.60 | 345.60 | 345.60 | 345.60 | 345.60 | 345.60 | 345.60 | 345.60 | 345.60 | 306.56 | 52.92 |
| C3H8 | 44.09 | 10.45 | 205.20 | 205.20 | 205.20 | 205.20 | 205.20 | 205.20 | 205.20 | 205.20 | 205.20 | 205.20 | 182.20 | 77.17 |
| IC4H10 | 58.12 | 12.41 | 108.00 | 108.00 | 108.00 | 108.00 | 108.00 | 108.00 | 108.00 | 108.00 | 108.00 | 108.00 | 95.80 | 58.40 |
| NC4H10 | 58.12 | 11.95 | 97.20 | 97.20 | 97.20 | 97.20 | 97.20 | 97.20 | 97.20 | 97.20 | 97.20 | 97.20 | 86.22 | 58.41 |
| IC5H12 | 72.15 | 13.88 | 118.80 | 118.80 | 118.80 | 118.80 | 118.80 | 118.80 | 118.80 | 118.80 | 118.80 | 118.80 | 105.38 | 89.00 |
| TOTAL | | | 1080.00 | 1080.00 | 1080.00 | 1080.00 | 1080.00 | 1080.00 | 1080.00 | 1080.00 | 1080.00 | 1080.00 | 958.00 | 349.42 |
| TEMPERATURE DEG F | | | 80.0 | 80.0 | 166.8 | 120.0 | 120.0 | 210.7 | 210.7 | 163.0 | 163.0 | 120.0 | −115.8 | 120.0 |
| PRESSURE PSIA | | | 60.0 | 60.0 | 149.0 | 145.0 | 145.0 | 350.0 | 350.0 | 345.0 | 345.0 | 340.0 | 70.0 | 340.0 |
| TOTAL ENIHAL MMBTU/HR | | | 6.401 | 6.401 | 7.852 | 6.919 | 6.919 | 8.328 | 8.328 | 6.989 | 6.989 | 4.222 | −3.573 | .283 |
| SPECF ENTHAL BTU/LB | | | 150.49 | 150.49 | 184.61 | 162.68 | 162.68 | 195.80 | 195.00 | 164.32 | 164.32 | 99.27 | −94.72 | 15.45 |
| PSEUDO TC DEG F | | | 128.1 | 128.2 | 128.2 | 128.2 | 128.2 | 128.2 | 128.2 | 128.2 | 128.2 | 128.2 | 128.2 | 239.4 |
| PSEUDO PC PSIA | | | 635.5 | 635.5 | 635.5 | 635.5 | 635.5 | 635.5 | 635.5 | 635.5 | 635.5 | 635.5 | 635.5 | 578.5 |
| PSEUDO TR | | | .918 | .918 | 1.066 | .986 | .986 | 1.140 | 1.140 | 1.059 | 1.059 | .986 | .585 | .829 |
| PSUEDO PR | | | .094 | .094 | .234 | .228 | .228 | .551 | .551 | .543 | .543 | .535 | .110 | .588 |
| PSEUDO ACENT | | | .118 | .118 | .118 | .118 | .118 | .118 | .118 | .118 | .118 | .118 | .118 | .167 |
| LVOL/MOL @ 60 F GAL/MOL | | | 0.00 | 0.00 | 0.00 | 0.00 | 0.00 | 0.00 | 0.00 | 0.00 | 0.00 | 0.00 | 0.00 | 11.62 |
| STP GAS VOL MMSCFD | | | 9.867 | 9.867 | 9.867 | 9.867 | 9.867 | 9.867 | 9.867 | 0.0000 | 0.0000 | 0.0000 | 0.0000 | 0.000 |
| DENSITY @ T,P LB/CUFT | | | .5291 | .5291 | 1.1320 | 1.1905 | 1.1905 | 2.4850 | 2.4850 | 0.0000 | 0.0000 | 0.0000 | 0.0000 | 33.4649 |
| SPEC GRAV | | | 1.3594 | 1.3594 | 1.3594 | 1.3594 | 1.3594 | 1.3594 | 1.3594 | 0.0000 | 0.0000 | 0.0000 | 0.0000 | .5408 |
| LVOL/MIN @ 60 F GAL/MIN | | | 0.00 | 0.00 | 0.00 | 0.00 | 0.00 | 0.00 | 0.00 | 0.00 | 0.00 | 0.00 | 0.00 | 67.70 |
| LVOL/MIN @ T,P GAL/MIN | | | 0.00 | 0.00 | 0.00 | 0.00 | 0.00 | 0.00 | 0.00 | 0.00 | 0.00 | 0.00 | 0.00 | 68.24 |
| GVOL/MIN @ T,P CUFT/MIN | | | 1339.68 | 1339.68 | 626.20 | 595.44 | 595.44 | 285.27 | 287.27 | 0.00 | 0.00 | 0.00 | 0.00 | 0.00 |
| Z(SRK) | | | .7709 | .7709 | .7709 | .7709 | .7709 | .7709 | .7709 | 0.0000 | 0.0000 | 0.0000 | 0.0000 | .0257 |
| MASS LB | | | 42532.5 | 42532.5 | 42532.5 | 42532.5 | 42532.5 | 42532.5 | 42532.5 | 42532.5 | 42532.5 | 42532.5 | 37727.9 | 18314.3 |
| MOL WT LB/LBMOL | | | 39.382 | 39.382 | 39.382 | 39.382 | 39.382 | 39.382 | 39.382 | 39.382 | 39.382 | 39.382 | 39.382 | 52.413 |

STREAM

TABLE III-continued

| COMP | M.W. | G/MOL | 43 (V) | 80 (2) | 86 (L) | 44 (V) | 84 (V) | 52 (2) | 56 (2) | 54 (2) | 60 (L) | 88 (2) | 72 (V) | 66 (2) |
|---|---|---|---|---|---|---|---|---|---|---|---|---|---|---|
| | | | | | | | FLOW RATES LBMOL/HR (PHASE) | | | | | | | |
| CH4 | 16.04 | 6.42 | 191.69 | 205.20 | 72.27 | 191.69 | 132.93 | 205.20 | 23.18 | 182.02 | 182.02 | 205.20 | 23.18 | 23.18 |
| C2H4 | 28.05 | 9.66 | 292.68 | 345.60 | 302.98 | 292.68 | 42.62 | 345.60 | 39.04 | 306.56 | 306.56 | 345.60 | 39.04 | 39.04 |
| C3H8 | 44.09 | 10.45 | 128.03 | 205.20 | 203.95 | 128.03 | 1.25 | 205.20 | 23.18 | 182.02 | 182.02 | 205.20 | 23.18 | 23.18 |
| IC4H10 | 58.12 | 12.41 | 49.60 | 108.00 | 107.88 | 49.60 | .12 | 108.00 | 12.20 | 95.80 | 95.80 | 108.00 | 12.20 | 12.20 |
| NC4H10 | 58.12 | 11.95 | 38.79 | 97.20 | 97.15 | 38.79 | .05 | 97.20 | 10.98 | 96.22 | 86.22 | 97.20 | 10.98 | 10.98 |
| IC5H12 | 72.15 | 13.88 | 29.80 | 118.80 | 118.79 | 29.80 | .01 | 118.80 | 13.42 | 105.38 | 105.38 | 118.80 | 13.42 | 13.42 |
| TOTAL | | | 730.58 | 1080.00 | 903.01 | 730.58 | 176.99 | 1080.00 | 122.00 | 958.00 | 958.00 | 1080.00 | 122.00 | 122.00 |
| TEMPERATURE DEG F | | | 120.0 | -113.0 | -113.0 | 120.0 | -113.0 | 120.0 | 120.0 | 120.0 | -92.0 | -113.0 | -66.1 | -99.6 |
| PRESSURE PSIA | | | 340.0 | 70.0 | 70.0 | 339.0 | 70.0 | 340.0 | 339.0 | 339.0 | 335.0 | 70.0 | 335.0 | 70.0 |
| TOTAL ENTHAL MMBTU/HR | | | 3.939 | -3.928 | -4.388 | 3.941 | .460 | 4.222 | .478 | 3.753 | -3.573 | -3.928 | -.387 | -.387 |
| SPECF ENTHAL BTU/LB | | | 162.65 | -92.36 | -112.12 | 162.72 | 135.50 | 99.27 | 99.47 | 99.47 | -94.72 | -92.36 | -80.56 | -80.56 |
| PSUEDO TC DEG F | | | 75.0 | 128.2 | 167.8 | 75.0 | -74.0 | 128.2 | 128.2 | 128.2 | 128.2 | 128.2 | 128.2 | 128.2 |
| PSEUDO PC PSIA | | | 662.7 | 635.5 | 625.5 | 662.7 | 686.4 | 635.5 | 635.5 | 635.5 | 635.5 | 635.5 | 635.5 | 635.5 |
| PSEUDO TR | | | 1.084 | .590 | .552 | 1.084 | .899 | .986 | .986 | .986 | .625 | .590 | .669 | .613 |
| PSEUDO PR | | | .513 | .110 | .112 | .512 | .102 | .535 | .533 | .533 | .527 | .110 | .527 | .110 |
| PSEUDO ACENT | | | .094 | .118 | .135 | .094 | .026 | .118 | .118 | .118 | .118 | .118 | .118 | .118 |
| LVOL/MOL @ GAL/MOL | | | 0.00 | 0.00 | 10.71 | 0.00 | 0.00 | 0.00 | 0.00 | 0.00 | 10.14 | 0.00 | 10.14 | 0.00 |
| STP GAS VOL MMSCFD | | | 6.675 | 0.000 | 0.000 | 6.675 | 1.617 | 0.000 | 0.000 | 0.000 | 0.000 | 0.000 | 0.000 | 0.000 |
| DENSITY @ T,P LB/CUFT | | | 2.1368 | 0.0000 | 31.8604 | 2.1305 | .3795 | 0.0000 | 0.0000 | 0.0000 | 30.6430 | 0.0000 | 30.4325 | 0.0000 |
| SPEC GRAV | | | 1.1443 | 0.0000 | .4855 | 1.1443 | .6620 | 0.0000 | 0.0000 | 0.0000 | .4659 | 0.0000 | .4659 | 0.0000 |
| LVOL/MIN @ 60 F GAL/MIN | | | 0.00 | 0.00 | 161.17 | 0.00 | 0.00 | 0.00 | 0.00 | 0.00 | 161.89 | 0.00 | 20.62 | 0.00 |
| LVOL/MIN @ T,P GAL/MIN | | | 0.00 | 0.00 | 153.16 | 0.00 | 0.00 | 0.00 | 0.00 | 0.00 | 153.51 | 0.00 | 19.68 | 0.00 |
| GVOL/MIN @ T,P CUFT/MIN | | | 188.90 | 0.00 | 0.00 | 189.46 | 149.05 | 0.00 | 0.00 | 0.00 | 153.51 | 0.00 | 19.68 | 0.00 |
| Z(SRK) | | | .8478 | 0.0000 | .0223 | .8478 | .9506 | 0.0000 | 0.0000 | 0.0000 | .0211 | 0.0000 | .2011 | 0.0000 |
| MASS LB | | | 24218.2 | 42532.5 | 39138.4 | 24218.2 | 3394.2 | 42532.5 | 4804.6 | 37727.9 | 37727.9 | 42532.5 | 4804.6 | 4804.6 |
| MOL WT LB/LBMOL | | | 33.149 | 39.382 | 43.342 | 33.149 | 19.177 | 39.382 | 39.382 | 39.382 | 39.382 | 39.382 | 39.382 | 39.382 |

TABLE IV

COLUMN PROFILES

| RAY NO. | TEMP. DEF F | LIQUID RATES LBMOL/HR | LIQUID RATES LB/HR | VAPOR RATES LBMOL/HR | VAPOR RATES LB/HR |
|---|---|---|---|---|---|
| 0 | −111.37 | 0. | 0. | 701.9 | .1198E + 05 |
| 1 F | −108.57 | 341.8 | 7384. | 505.9 | 8607. |
| 2 | −93.71 | 294.4 | 6970. | 467.1 | 8187. |
| 3 | −72.59 | 264.4 | 6834. | 419.7 | 7773. |
| 4 G | −51.70 | 210.2 | 5782. | 389.8 | 7637. |
| 5 | −48.00 | 195.6 | 5465. | 335.6 | 6585. |
| 6 F | −27.35 | 534.2 | .1758E + 05 | 236.5 | 4749. |
| 7 | 11.63 | 578.0 | .1980E + 05 | 250.4 | 5867. |
| 8 G | 51.48 | 514.5 | .1859 + 05 | 294.2 | 8093. |
| 9 | 70.47 | 552.6 | .2023E + 05 | 230.7 | 6883. |
| 10 | 88.42 | 567.1 | .2134E + 05 | 268.8 | 8524. |
| 11 | 116.87 | 283.8 | .1171E + 05 | 283.3 | 9628. |

PROPERTIES WITHIN COLUMN

| RAY NO. | ENTHALPY BTU/LBMO LIQUID | ENTHALPY BTU/LBMO VAPOR | MOLECULAR WEIGHT LIQUID | MOLECULAR WEIGHT VAPOR |
|---|---|---|---|---|
| 0 | −5046. | −1860. | 21.358 | 17.067 |
| 1 | −5070. | −1839. | 21.602 | 17.012 |
| 2 | −5360. | −1700. | 23.673 | 17.526 |
| 3 | −5566. | −1523. | 25.844 | 18.519 |
| 4 | −5643. | −1367. | 27.501 | 19.595 |
| 5 | −5712. | −1333. | 27.938 | 19.624 |
| 7 | −5863. | −900.7 | 34.263 | 23.429 |
| 8 | −5293. | −657.8 | 36.138 | 27.508 |
| 9 | −4898. | −556.0 | 36.613 | 29.833 |
| 10 | −4596. | −416.7 | 37.625 | 31.704 |
| 11 | −4361. | −39.42 | 41.262 | 33.982 |

| | DENSITY LB/FT$^3$ | | VISCOSITY CP | |
|---|---|---|---|---|
| | LIQUID | VAPOR | LIQUID | VAPOR |
| 0 | 24.62 | 3.413 | .63758E − 01 | .91833E − 02 |
| 1 | 24.78 | 3.356 | .64245E − 01 | .91664E − 02 |
| 2 | 26.42 | 3.174 | .70778E − 01 | .92980E − 02 |
| 3 | 27.51 | 3.053 | .74628E − 01 | .95785E − 02 |
| 4 | 27.78 | 3.007 | .75237E − 01 | .98624E − 02 |
| 5 | 27.83 | 2.967 | .76227E − 01 | .98803E − 02 |
| 6 | 30.08 | 2.794 | .90108E − 01 | .10084E − 01 |
| 7 | 29.06 | 3.074 | .79961E − 01 | .10683E − 01 |
| 8 | 28.01 | 3.530 | .71689E − 01 | .11243E − 01 |
| 9 | 27.13 | 3.901 | .66276E − 01 | .11539E − 01 |
| 10 | 26.56 | 4.175 | .63034E − 01 | .11781E − 01 |
| 11 | 26.97 | 4.253 | .64494E − 01 | .12019E − 01 |

VISCOSITY CALCULATED BY METHOD OF DEAN AND STIEL FOR NON POLAR GASES (REF. J. AICHE (1965))

ALTERNATE EMBODIMENT

Figure 3:
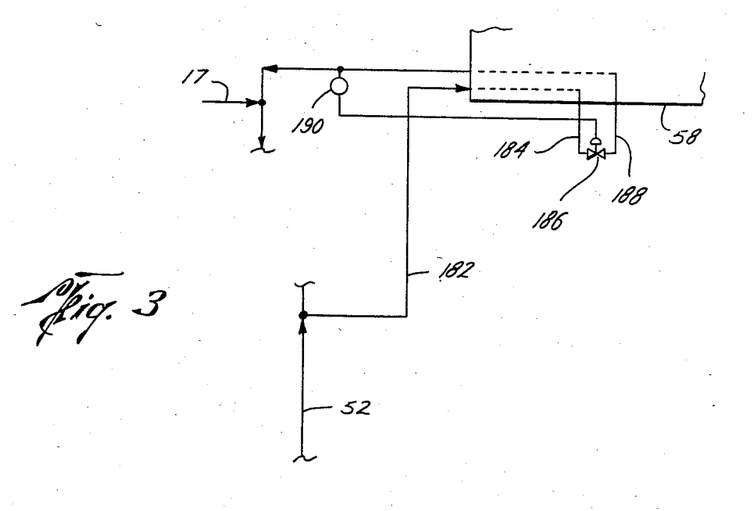
FIG. 3 is a partial flow diagram of a second, non-preferred, embodiment of the present invention.

The refrigerant streams may be altered within the spirit of the invention to produce a cascade system for an alternate embodiment. In the alternate embodiment partially shown in FIG. 3, all of the reference numerals correspond to those of FIG. 1, except references 182, 184, 186, 188, 190, and 192 which have been added As shown in FIG. 3, a portion of the refrigerant in stream 52 is fed to refrigerant/feed exchanger 58 via stream 182, where it is cooled and the fluid condensed at an intermediate level of temperature of 0° F. to −60° F. This refrigerant exits exchanger 58 in stream 184. Stream 184 flows into valve 186 where the pressure is reduced to an intermediate pressure level of 60 to 180 psia, producing temperatures in valve outlet stream 188 which are 5° F. to 30° F. colder than the high pressure stream 18 The rate of refrigerant through streams 182, 184, 188 is regulated by valve 186 which is opened and closed by flow instrument sensor/contoller 190 The amount valve 186 is opened or closed depends on whether the flow in stream 192 as measured by sensor 190 is below or above predtermined set point. The refrigerant exits the valve 186 in stream 1BB and returns to the exchanger 58. In exchanger 58, the refrigerant evaporates, contributing refrigerant energy to the incoming feed streams This refrigerant exits the exchanger 58 in stream 192, where it rejoins refrigerant stream 17 at the discharge of the first stage refrigerant after-cooler Because many varying and different embodiments may be made within the scope of the inventive concept herein taught including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed as invention is:

1. A process for separating methane from substantial amounts of heavier hydrocarbons in a mixed gas, comprising:

A. Cooling the mixed gas in a indirect heat exchanger with a mixed refrigerant;

B. Compressing the refrigerant in two stages of compressors;

C. Separating the methane from substantial amounts of heavier hydrocarbons of the mixed gas in a distillation column using the compressed refrigerant to provide heat energy for the distillation, such refrigerant supplying such heat energy prior to the cooling in Step A;

D. Splitting the compressed refrigerant from step C into two portions;

E. Supplying a first portion of the compressed refrigerant of Step C for cooling in Step A;

F. Supplying a second portion of the compressed refrigerant of Step C to provide heat energy for the distillation prior to the cooling in Step A;

G. Supplying the second portion of the compressed refrigerant of Step F for cooling in Step A;

H. Feeding the first portion of the compressed refrigerant of Step E to the second stage compressor; and I. Feeding the second portion of the compressed refrigerant of Step G to the first stage compressor 2. Apparatus for separating methane from substantial amounts of heavier hydrocarbons in a mixed gas, comprising:

Indirect heat exchange means for cooling the mixed gas in a indirect heat exchanger with a mixed refrigerant;

Compression means including a first and a second stage compressor for compressing the refrigerant;

Distillation column means for separating the methane from substantial amounts of heavier hydrocarbons of the mixed gas, said distillation column means including heat exchange reboiler means for using the compressed refrigerant to provide heat energy for the distillation, such refrigerant supplying such heat energy prior to the cooling in said indirect heat exchanger;

Means for splitting the compressed refrigerant from said heat exchange reboiler means into two portions; each having the same composition;

First supply means for supplying a first portion of the compressed refrigerant from said heat exchange reboiler mean to said indirect heat exchange means;

Second supply means for supplying a second portion of the compressed refrigerant from said heat exchange reboiler means to provide heat energy to said distillation column means;

Third supply means for supplying the second portion of the compressed refrigerant from said second supply means to said indirect heat exchange means;

Means for feeding the first portion of the refrigerant from said indirect heat exchange means to said second stage compressor; and Means for feeding the second portion of the refrigerant from said indirect heat exchanger to said first stage compressor.

* * * * *